(12) United States Patent
Lubin et al.

(10) Patent No.: US 11,301,703 B2
(45) Date of Patent: Apr. 12, 2022

(54) ROBUST BIOMETRIC ACCESS CONTROL BASED ON DYNAMIC STRUCTURAL CHANGES IN TISSUE

(71) Applicant: SRI International, Menlo Park, CA (US)

(72) Inventors: Jeffrey Lubin, Princeton, NJ (US); James R. Bergen, Pennington, NJ (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 16/487,053

(22) PCT Filed: Mar. 21, 2018

(86) PCT No.: PCT/US2018/023606
§ 371 (c)(1),
(2) Date: Aug. 19, 2019

(87) PCT Pub. No.: WO2018/175616
PCT Pub. Date: Sep. 27, 2018

(65) Prior Publication Data
US 2020/0342245 A1 Oct. 29, 2020

Related U.S. Application Data

(60) Provisional application No. 62/474,500, filed on Mar. 21, 2017.

(51) Int. Cl.
*G06K 9/00* (2006.01)
*G07C 9/37* (2020.01)

(52) U.S. Cl.
CPC ....... *G06K 9/00906* (2013.01); *G06K 9/0061* (2013.01); *G06K 9/00107* (2013.01); *G06K 9/00288* (2013.01); *G07C 9/37* (2020.01)

(58) Field of Classification Search
CPC ........... G06K 9/00906; G06K 9/00107; G06K 9/00288; G06K 9/0061;
(Continued)

(56) References Cited

U.S. PATENT DOCUMENTS 7,751,862 B2 7/2010 Hogan
8,856,541 B1 * 10/2014 Chaudhury ........ G06K 9/00912
713/186

(Continued)

OTHER PUBLICATIONS

International Search Report and Written Opinion of International Application No. PCT/US2018/023606, dated May 31, 2018, 14 pp.
(Continued)

*Primary Examiner* — Siamak Harandi
(74) *Attorney, Agent, or Firm* — Moser Taboada

(57) ABSTRACT

A biometric access control system for controlling access to an environment based on an authorization status of a living subject is disclosed. In one example, a data source generates image data of a tissue region of the subject. A liveness measurement unit processes the image data to detect changes over at least one of time or spatial volume in one or more structural features of the tissue region and generates, based on the detected changes, a spoofing attack detection status indicating that the image data is from living biological tissue or that a spoofing attack is detected. A biometric identification unit processes at least a portion of the same image data generated by the data source to generate biometric information indicative of an identity of the subject. Responsive to the spoofing attack detection status and the biometric information, an authorization unit outputs an authorization status for the subject.

20 Claims, 7 Drawing Sheets

(58) Field of Classification Search
CPC ..... G06K 2009/00939; G06K 9/00892; G07C 9/37; A61B 5/117; A61B 5/024
See application file for complete search history.

(56) References Cited

U.S. PATENT DOCUMENTS

| | | | | |
|---|---|---|---|---|
| 10,817,722 | B1* | 10/2020 | Raguin | ............... A61B 3/102 |
| 10,820,840 | B2* | 11/2020 | Hogan | ............... G06K 9/00892 |
| 2012/0177257 | A1 | 7/2012 | Maev et al. | |
| 2013/0336547 | A1 | 12/2013 | Komogortsev | |
| 2014/0044321 | A1* | 2/2014 | Derakhshani | ............ G06K 9/00 382/117 |
| 2016/0019410 | A1 | 1/2016 | Komogortsev | |
| 2016/0140390 | A1 | 5/2016 | Ghosh et al. | |
| 2016/0232401 | A1 | 8/2016 | Hoyos et al. | |
| 2016/0335483 | A1 | 11/2016 | Pfursich et al. | |
| 2017/0048244 | A1 | 2/2017 | Loughlin-McHugh et al. | |
| 2018/0218200 | A1* | 8/2018 | Wolf | ............... G06K 9/00288 |
| 2018/0247146 | A1* | 8/2018 | Riddle | ............... G06K 9/4661 |

OTHER PUBLICATIONS

International Preliminary Report on Patentability from International Application No. PCT/US2018/023606, dated Oct. 3, 2019 13 pp.
"Odin," IARPA, Office of the Director of National Intelligence, Retrieved from https://www.iarpa.gov/index.php/research-programs/odin/odin-baa, Jun. 16, 2016, 3 pp.
"Biometrics," NIST, Retrieved from: https://web.archive.org/web/20170713225024/https:/www.nist.gov/programs-projects/biometrics, Jul. 15, 2017, 4 pp.
"Fingerprint," NIST, Retrieved from: https://web.archive.org/web/20170714074209/https:/www.nist.gov/programs-projects/fingerprint, Jul. 15, 2017, 4 pp.
"Fingerprint Recognition," NIST, Retrieved from: https://web.archive.org/web/20170714074256/https:/www.nist.gov/programs-projects/fingerprint-recognition, Jul. 15, 2017, 4 pp.
Next Generation Fingerprint Technologies NIST, Retrieved from: https://web.archive.org/web/20170715232604/https:/www.nist.gov/programs-projects/next-generation-fingerprint-technologies, Jul. 15, 2017, 2 pp.
Allen, "Photoplethysmography and its application in clinical physiological measurement," Physiological measurement: Topical Review, 28(3) R1-R39, Feb. 2007, 39 pp.
Allen et al., Microvascular blood flow and skin temperature changes in the fingers following a deep inspiratory gasp. Physiol Meas. 23, Mar. 2002, pp. 365-373.
Allen et al., Similarity in bilateral photoplethysmographic peripheral pulse wave characteristics at the ears, thumbs and toes. Physiol Meas. 21, May 2000, pp. 369-377.
Amer et al., "Deep Multimodal Fusion: A Hybrid Approach," Int J Comput Vis. 126, Apr. 2018, pp. 440-456.
Amer et al., "Human Social Interaction Modeling Using Temporal Deep Networks," CoRR, May 2015, 11 pp.
Amer et al., "Multimodal fusion using dynamic hybrid models," IEEE Winter Conference on Applications of Computer Vision, Mar. 2014, 8 pp.
Amer et al., "Emotion Detection in Speech using Deep Networks," 2014 IEEE International Conference on Acoustics, Speech and Signal Processing (ICASSP), May 2014, 5 pp.
Anjos et al., "Motion-based counter-measures to photo attacks in face recognition," IET Biometrics 3 (3), Sep. 2014, 27 pp.
Arif et al., "Physical Activities Monitoring Using Wearable Acceleration Sensors Attached to the Body," PLoS ONE, 10(7), e0130851, Jul. 23, 2015, 16 pp.
Belhumeur et al., "Localizing parts of faces using a consensus of exemplars," Proceedings of the 24th IEEE Conference on Computer Vision and Pattern Recognition (CVPR), Jun. 2011. 8 pp.
Chang et al., "Fingerprint Spoof Detection by NIR Optical Analysis," State of the Art in Biometrics; Chapter 3, IntechOpen, Jul. 2011, 25 pp.
Tan et al., "Integrating ocular and Iris descriptors for fake iris image detection," IEEE; 2nd International Workshop on Biometrics and Forensics, Mar. 2014, 4 pp.
Czajka, "Pupil dynamics for liveness detection," IEEE Transactions on Information Forensics and Security; 10(4), Apr. 2015, pp. 726-735.
De Zambotti et al., "K-Complexes: Interaction between the Central and Autonomic Nervous Systems during Sleep,". Sleep;39(5), May 2016, pp. 1129-1137.
De Zambotti et al., "Measures of sleep and cardiac functioning during sleep using a multi-sensory commercially-available wristband in adolescents," Physiol Behav. May 2016, 17 pp.
Ehrlich et al., "Facial Attributes Classification using Multi-Task Representation Learning," IEEE Conference on Computer Vision and Pattern Recognition (CVPR, Jun. 2016, pp. 47-55.
Einhäuser et al., Pupil dilation betrays the timing of decisions. Frontiers in Human Neuroscience: 4:18, Feb. 2010, 9 pp.
Escalera et al., "ChaLearn Looking at People Challenge 2014: Dataset and Results," ECCV 2014 Workshops; Part 1, Mar. 2015, 15 pp.
Gavish et al., "Blood pressure variation in response to changing arm cuff height cannot be explained solely by the hydrostatic effect," Journal of Hypertension; 29(11), Jul. 2011, pp. 2099-2104.
Hickey et al., "Investigation of peripheral photoplethysmographic morphology changes induced during a hand-elevation study," J Clin Monit Comput. Aug. 2015, 10 pp.
Hinton et al., "A fast learning algorithm for deep belief nets," Neural Computation; 18(7), Jul. 2006, pp. 1527-1554.
Hinton, "Training products of experts by minimizing contrastive divergence," Neural Computation; 14(8), Aug. 2002, pp. 1771-1800.
Hochreiter et al., "Long Short-Term Memory," Technical Report FKI-207-95, Aug. 21, 1995, 8 pgs.
Hollingsworth et al., "Pupil dilation degrades iris biometric performance," Computer Vision and Image Understanding; 113, Jan. 2009, pp. 150-157.
Inan et al., (2015) "Unobtrusive Monitoring of Cardiovascular Health at Home Using a Modified Weighing Scale," Springer International Publishing, In 6th European Conference of the International Federation for Medical and Biological Engineering, Sep. 7-11, 2014, pp. 918-921.
Kammila et al., "Systematic error in the determination of nocturnal blood pressure dipping status by ambulatory blood pressure monitoring," Blood Pressure Monitoring; 7(2), Apr. 2002, pp. 131-134.
Lang et al., "Emotion, attention, and the startle reflex," Psychological review; 97(3), Jul. 1990, pp. 377-395.
Larochelle et al., "Classification using discriminative Restricted Boltzmann Machines," ICML '08: Proceedings of the 25th International Conference on Machine Learning, Jul. 2008, 8 pp.
Nagano et al., "Skin microstructure deformation with displacement map convolution," ACM Transactions on Graphics (TOG); 34(4), Article 109, Aug. 2015, 10 pp.
Ngiam et al., "Multimodal Deep Learning," ICML'11: Proceedings of the 28th International Conference on International Conference on Machine Learning, Jun. 2011, 8 pp.
Ohmi et al., "Dynamic analysis of internal and external mental sweating by optical coherence tomography," Journal of Biomedical Optics; 14(1), Jan./Feb. 2009, 7 pp.
Raghavan et al., "GPU Activity Prediction using Representation Learning," Proceedings of the 33rd International Conference on Machine Learning, Mar. 27, 2017, 5 pp.
Raghavendra et al., "Presentation Attack Detection Algorithm for Face and Iris Biometrics," 22nd European Signal Processing Conference (EUSIPCO), Sep. 1-5, 2014, 5 pp.
Siddiquie et al., "The Tower Game Dataset: A multimodal dataset for analyzing social interaction predicates," 2015 International Conference on Affective Computing and Intelligent Interaction (ACII), Sep. 21-24, 2015, 8 pp.
Schroff et al., "Facenet: A unified embedding for face recognition and clustering," In Proceedings of the IEEE Conference on Computer Vision and Pattern Recognition (CVPR), Jun. 2015, pp. 815-823.

(56) References Cited

OTHER PUBLICATIONS

Schuckers, "Liveness detection: Fingerprint," Encyclopedia of Biometrics, Springer, 2009, 7pp. (Applicant points out, in accordance with MPEP 609.04(a), that the year of publication, 2009 is sufficiently earlier than the effective U.S. filing date, so that the particular month of publication is not in issue.).

Shields et al., "Action-Affect Classification and Morphing using Multi-Task Representation Learning," ECCV, Mar. 2016, 19 pp.

Smith et al., "The heart rate response to a brief auditory and visual stimulus," *Psychophysiology*, 6(3), Nov. 1969, pp. 317-329.

Snoek et al., "Practical Bayesian Optimization of Machine Learning Algorithms," Neural Information Processing Systems (NIPS), Jun. 2012, 9 pp.

Srivastava et al., "Multimodal learning with Deep Boltzmann Machines," Neural Information Processing Systems (NIPS), 2012, 9 pp. (Applicant points out, in accordance with MPEP 609.04(a), that the year of publication, 2012 is sufficiently earlier than the effective U.S. filing date, so that the particular month of publication is not in issue.).

Starr et al., "Studies on the estimation of cardiac output in man, and of abnormalities in cardiac function from the heart's recoil and the blood's impact: the ballistocardiogram," The American Journal of Physiology; 127(1), Aug. 1, 1939, 28 pp.

Steinhauer et al., "Pupillary dilation to emotional visual stimuli revisited," Psychophysiology; 20(4) SPR Abstracts, Jul. 1983, pp. 472.

Sutskever et al., "The Recurrent Temporal Restricted Boltzmann Machine," Proceedings of the Twenty-Second Annual Conference on Neural Information Processing Systems (NIPS), Dec. 8-11, 2008, 8 pp.

Sutskever et al., "Learning multilevel distributed representations for high-dimensional sequences," Proceedings of the Eleventh International Conference on Artificial Intelligence and Statistics (AISTATS), Mar. 21-24, 2007, 8 pp.

Taylor et al., "Two distributed-state models for generating high-dimensional time series," Journal of Machine Learning Research (JMLR), Mar. 2011, pp. 1025-1068.

Vicente et al., "Driver Gaze Tracking and Eyes Off the Road Detection System," IEEE Transactions on Intelligent Transportation Systems; 16(4), Aug. 2015, pp. 2014-2027.

Vila et al., "Cardiac defense: From attention to action," International Journal of Psychophysiology; 66(3), Dec. 2007, pp. 169-182.

Wang et al., Face Re-Lighting from a Single Image under Harsh Lighting Conditions, 07' IEEE Conference on Computer Vision and Pattern Recognition (CVPR), Jun. 17-22, 2007, 8 pp.

Wei et al., "Counterfeit iris detection based on texture analysis," 19th International Conference on Pattern Recognition. Dec. 8-11, 2008, 4 pp.

Wilkins et al., "The effect of the dependent position upon blood flow in the limbs," Circulation; 2(3), Sep. 1950, pp. 373-379.

Xiong et al., "Supervised Descent Method and its Applications to Face Alignment," IEEE Conference on Computer Vision and Pattern Recognition (CVPR), Jun. 2013, pp. 532-539.

Hochreiter et al., "Long Short-Term Memory," Neural Computation; 9(8):1735-1780, Nov. 15, 1997, 32 pp.

\* cited by examiner

ROBUST BIOMETRIC ACCESS CONTROL BASED ON DYNAMIC STRUCTURAL CHANGES IN TISSUE

This application is a national stage application under 35 U.S.C. § 371 of International Application No. PCT/US2018/023606 by Lubin et al., entitled "ROBUST BIOMETRIC ACCESS CONTROL BASED ON DYNAMIC STRUCTURAL CHANGES IN TISSUE" and filed on Mar. 21, 2018, which claims the benefit of U.S. Provisional Application No. 62/474,500 by Lubin et al., entitled "PHYSIOLOGICAL DYNAMICS-BASED DETECTION OF LIVENESS, SPOOFING, OR PRESENTATION ATTACKS" and filed on Mar. 21, 2017. The entire contents of Application Nos. PCT/US2018/023606 and 62/474,500 are incorporated herein by reference.

The invention was made with Government support. The Government has certain rights in the invention.

TECHNICAL FIELD

This disclosure relates generally to biometric systems, and more specifically to techniques and systems that verify liveness for detecting spoofing or presentation attacks on biometric systems.

BACKGROUND

Biometric security refers to use of human characteristics to authorize, identify, detect, or screen for a particular person or persons. Biometric security typically involves the use of characteristics that are unique to an individual, such as fingerprints, hand prints, voice prints, facial features, eye irises/retinas, or a combination of the foregoing, to distinguish the individual from other people. Biometric security may provide more stringent access control than conventional security systems, such as typed passwords or physical key-and-lock systems, because biometric characteristics cannot be misplaced and generally cannot be shared with other individuals. Biometric security may be particularly important to security-conscious institutions, such as local, regional, and federal governments, corporations, transit authorities such as airports, train stations, and shipping ports, or to medical institutions such as hospitals and clinics.

SUMMARY

In general, the disclosure describes techniques, systems, and devices for using changes in structural features of tissue for biometric access control. More specifically, robust biometric access control systems are described that generate image data of a tissue region of a living subject. A biometric access control system processes the image data of the tissue region to determine whether the image data was captured from living, biological tissue. For example, the biometric access control system may analyze changes in one or more structural features of the tissue region that occur over time, over a spatial volume, or a combination of both, to determine whether the one or more structural features exhibit characteristics of living, biological tissue. As a further example, the biometric access control system may analyze curtaining and folding of an iris of an eye of the subject that occur over time, wrinkling and stretching of skin regions of a face of the subject that occur over time, or changes between dermal layers of a deep fingerprint of the subject that occur over a spatial volume. As a further example, the biometric access control system may control delivery of a stimulus to the subject and compare changes in the one or more structural features that occur in response to the stimulus to responses expected of living, biological tissue to the stimulus. By analyzing the changes in the structural features that occur over time or over a spatial region, a potential attacker would have to create extremely detailed artificial tissue that accurately mimicked the behavior of living, biological tissue at a very high level of granularity to defeat the biometric access control system. Such simulation may be impractical or impossible to achieve. Therefore, the systems and techniques of the present disclosure may provide more robust biometric control access and provide a higher level of security against spoofing and/or presentation attacks over conventional systems that rely only on static imagery of tissue.

In one example, this disclosure describes a biometric access control system configured to control access to an environment based on an authorization status of a living subject, the biometric access control system including: a data source configured to generate image data of a tissue region of a subject; a liveness measurement unit configured to process the image data to detect changes over at least one of time or spatial volume in one or more structural features of the tissue region of the subject and generate, based on the detected changes in the one or more structural features, a spoofing attack detection status indicating that the image data is from living biological tissue from a living subject or that a spoofing attack is detected; a biometric identification unit configured to process at least a portion of the same image data generated by the data source for the tissue region of the subject to generate biometric information indicative of an identity of the subject; and an authorization unit configured to, responsive to the spoofing attack detection status and the biometric information indicative of the identity of the subject, output an authorization status for the subject.

In another example, this disclosure describes a biometric detection system including: a data source configured to generate image data of a tissue region of a subject; a liveness measurement unit configured to process the image data to detect changes over at least one of time or spatial volume in one or more structural features of the tissue region of the subject; a biometric information unit configured to process the detected changes in the one or more structural features of the tissue region of the subject over the at least one of time or spatial volume to generate biometric information for the subject and output the biometric information for the subject to an external biometric identification unit for processing to determine, based on the biometric information for the subject, an identity of the subject.

In another example, this disclosure describes a method for controlling access to an environment based on an authorization status of a living subject, the method including: generating, by a data source, image data of a tissue region of a subject; processing, by a liveness measurement unit, the image data to detect changes over at least one of time or spatial volume in one or more structural features of the tissue region of the subject; generating, by the liveness measurement unit and based on the detected changes in the one or more structural features, a spoofing attack detection status indicating that the image data is from living biological tissue from a living subject or that a spoofing attack is detected; processing, by a biometric identification unit, at least a portion of the same image data generated by the data source for the tissue region of the subject to generate biometric information indicative of an identity of the subject; and responsive to the spoofing attack detection status and the biometric information indicative of the identity of the subject, outputting, by an authorization unit, an authorization status for the subject.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
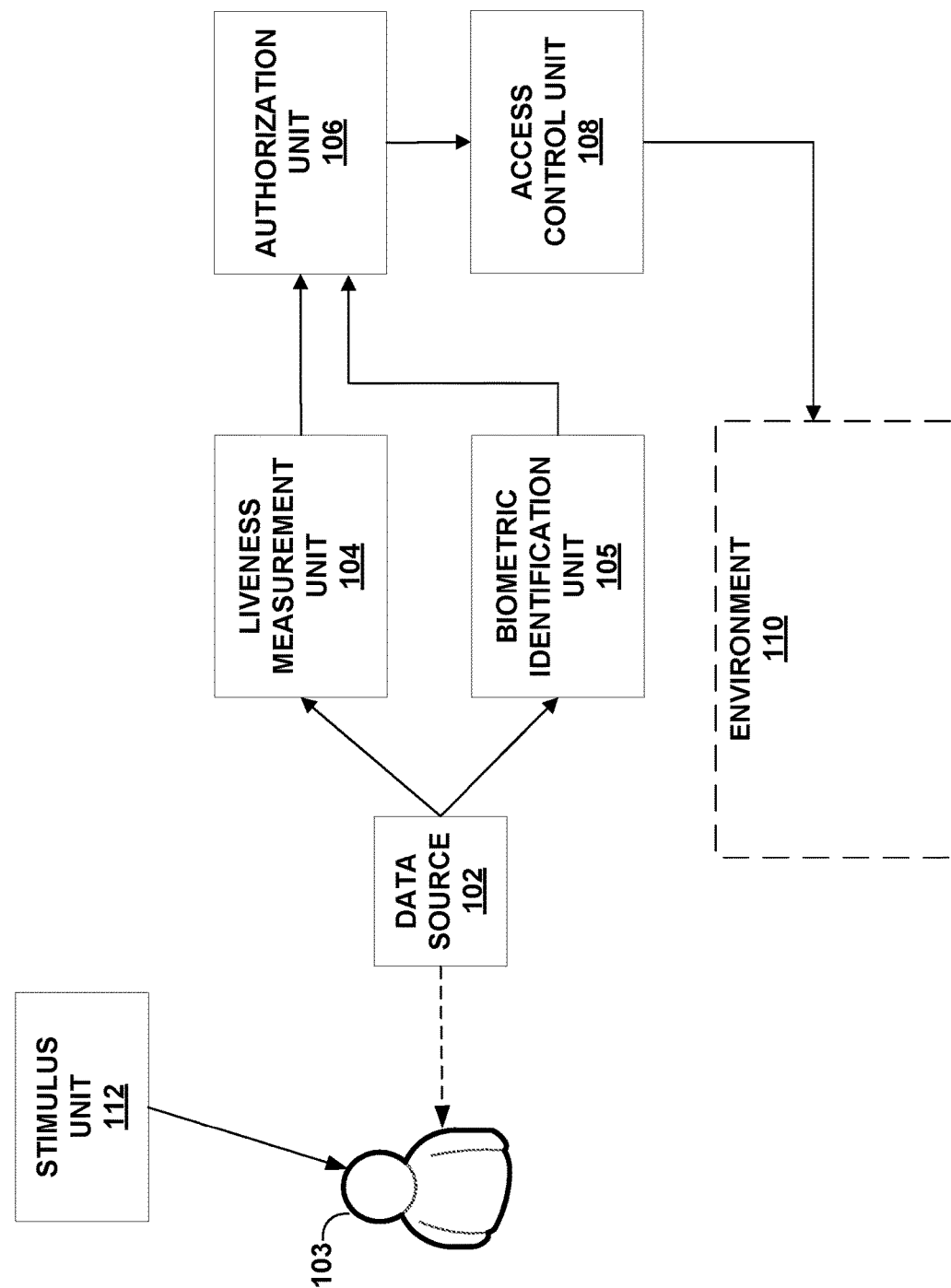
FIG. 1 is a block diagram illustrating an example biometric access control system for controlling access to an environment based on an authorization status of a human subject in accordance with the techniques of the disclosure.

Presentation attack detection (PAD) for fingerprint, face, and iris biometric systems has become a topic of increasing interest. There has been a rapid growth in the use of biometric techniques in security, commerce, and access control applications. A presentation attack on a biometric security system generally involves the presentation of a manufactured artifact, recorded data representation, or altered or dead tissue to a biometric sensor to "spoof" (e.g., gain unauthorized access to) the security system or environment to which the biometric security system controls access. PAD methods generally fall into two categories: (1) methods to detect specific identifying characteristics of artificial or altered objects presented to a biometric security system that are distinct from characteristics of real live users; and (2) methods to determine whether or not an object presented to a biometric security system behaves as living biological tissue.

Examples of the first type of PAD methods include detection of image texture, frequency, and intensity characteristics of printed irises and/or facial images that differ from those of signals captured from real irises and faces. Such methods include analysis using standard image texture features, detection of patterned contact lenses using similar techniques, and use of Cepstral and Binarized Statistical Image Features (also essentially texture-like descriptors) to detect printed photographs, masks, or video replays. Some systems may use an existing public database of real and spoofed biometric presentations to demonstrate that a technique may separate real presentations from spoof presentations. In contrast, liveness detection methods may focus on detecting characteristics in captured data that is absent from recorded or manufactured artifact presentations. Such techniques may involve detecting motion that is absent or unnatural in photographs or dead or artificial body parts, anatomical and physiological responses, such as pupil fluctuation or changes, finger deformation and/or blanching, or the use of advanced imaging techniques such as optical coherence tomography (OCT) or multispectral imaging to distinguish specific anatomical characteristics of human tissue. Conventional biometric security systems may rely on pattern recognition (e.g., fingerprint, iris pattern), which makes such security systems easy to defeat. Some conventional systems may further use photoplethysmographic detection of pulse, which may not provide increased security.

In accordance with the techniques, systems, and devices of the disclosure, a biometric access control system for controlling access to an environment based on an authorization status of a human subject is disclosed. In one example, the biometric access control system includes an image source configured to generate high-resolution image data of a tissue region of a subject. The biometric access control system includes a biometric identification unit that is configured to use at least a portion of the image data to generate biometric information indicative of an identity of the subject. For example, where the image data is of a finger or an eye of the subject, the biometric identification unit is configured to use the image data to generate biometric information, such as a unique fingerprint or iris scan, that is indicative of an identity of the subject. The biometric identification unit may determine the identity of the subject using the image data using methods such as pattern matching.

Furthermore, the biometric access control system may include a liveness measurement unit that is configured to process the high-resolution image data to detect changes in one or more structural features that are indicative of live human tissue. Such structural features may be smaller than one millimeter in size. In some examples, the changes to these structural features may occur over time. In other examples, the changes occur over a spatial volume (e.g., such as detecting changes in structural features across a dermal skin layer and one or more sub-surface or sub-dermal skin layers). Such dynamic changes in structural features (e.g., anatomical features of tissue) may be unique to live human tissue. Further, such dynamic changes may be impractical or impossible to replicate artificially using current technology to successfully spoof the biometric access control system. The liveness measurement unit may then generate, based on the detected changes to the structural features, a spoofing attack detection status that indicates whether the image data is from living biological tissue or a spoofing attack is detected.

The biometric access control system of the present disclosure is configured to use both the biometric identification generated by the biometric identification unit and the spoofing attack detection status generated by the liveness measurement unit to control access to an environment. For example, an authorization unit is configured to output an authorization status for the subject in response to the biometric identification and the and the spoofing attack detection status. An access control unit is configured to control access to the environment in response to the authorization status output received from the authorization unit. Accordingly, by using the techniques disclosed herein, a biometric access control system may verify that biometric information presented by a subject is obtained from live, human tissue prior to using the biometric information to authorize the subject to access an environment. Thus, a biometric access control system of the present disclosure may be less susceptible to presentation attacks and provide enhanced security over conventional biometric security systems that may only rely on static measurements of the subject. The biometric access control system may be configured to control physical access of the subject to the environment (e.g., control opening and closing of a door) or control access by identifying whether the subject entering an environment is authorized or not authorized to be present within the environment.

FIG. 1 is a block diagram illustrating example biometric access control system 100 for controlling access to environment 110 based on an authorization status of human subject 103 in accordance with the techniques of the disclosure. In one example, biometric access control system 100 includes data source 102, liveness measurement unit 104, biometric identification unit 105, authorization unit 106, and access control unit 108.

Data source 102 may be configured to generate image data of a tissue region of subject 103. In some examples, data source 102 is an image source, such as a digital camera, a smart phone with an integrated camera, or a photosensor. In some examples, data source 102 is a sensor that scans a one-dimensional line of spatial samples repeatedly over time to produce a spatiotemporal image. In some examples, data source 102 is a computer, a mobile device, a smart phone, a tablet, or a laptop that includes stored image data of the tissue region of subject 103. In some examples, data source 102 generates image data of structural features of the tissue region of subject 103. In some examples, data source 102 generates high-resolution image data of the tissue region of subject 103. As one example, data source 102 has sufficient resolution such that a size of the imaged structural features of the tissue region is within a range of greater than about one micrometer to less than about one millimeter. In another example, data source 102 has sufficient resolution such that a size of the imaged structural features of the tissue region is less than about one micrometer. In some examples, data source 102 generates two-dimensional image data of the tissue region, while in other examples, data source 102 generates three-dimensional image data of the tissue region. In some examples, data source 102 generates black and white image data. In other examples, data source 102 generates red-blue-green (RGB) or color image data. In further examples, data source 102 generates thermal image data, near infrared image (NIR) data, short-wave infrared (SWIR) image data, medium-wave infrared (MWIR) image data, or long-wave infrared (LWIR) image data. As one example, data source 102 generates hi-resolution three-dimensional OCT image tomography data, which image source provides to liveness measurement unit 104 for liveness detection as discussed below. In this example, data source 102 generates lower-resolution two-dimensional OCT image data, which data source 102 provides to biometric identification unit 105 for biometric identification as discussed below. In another example of the above, data source 102 provides the three-dimensional OCT image tomography data to biometric identification unit 105. In this example, biometric identification unit 105 applies a reductive transform to the three-dimensional OCT image tomography data to obtain two-dimensional OCT image tomography data with which to perform biometric identification.

In one example, data source 102 is an OCT device used for ophthalmological purposes. In another example, data source 102 is one or more off-the-shelf imaging sensors. In an example where data source 102 generates image data of an iris of subject 103, data source 102 includes a high frame rate NIR (near infrared) camera with sensitivity at 850 nanometer (nm) for iris penetration, and a 25-millimeter (mm) lens that enables macro-imagery. In an example where data source 102 generates image data of a face and/or skin of subject 103, data source 102 includes a high resolution RGB camera sufficient to capture detailed physiological facial features. In an example where data source 102 generates thermal image data of a head, neck, or face of subject 103 due to evaporative cooling from an alerting-related sweat response, data source 102 includes an LWIR low-resolution (e.g., 640×480 pixels) 60 frames per second (FPS) camera. In another example, data source 102 includes a LWIR sensor providing a thermal image of the face of subject 103 that provides information over time about the pattern of temperatures across a living face. In some examples, data source 102 includes a plurality of imaging sensors to provide a large pixel coverage of subject 103. In this example, the plurality of imaging sensors provide sufficient overlap to maximize signal-to-noise ratio (SNR) as well as correspondence in modality (e.g., feature correspondences in physiological measurements in LWIR and/or the visible spectrum).

Liveness measurement unit 104 may be configured to process the image data to detect changes in one or more structural features of the tissue region of subject 103. In some examples, liveness measurement unit 104 detects changes in the one or more structural features over time. In other examples, liveness measurement unit 104 detects changes in the one or more structural features over a spatial volume. The changes in the one or more structural features over the spatial volume may also take place over time. Liveness measurement unit 104 generates, based on the detected changes in the one or more structural features, a spoofing attack detection status. The spoofing attack detection status indicates either that the image data is from living biological tissue from a human subject or that a spoofing attack is detected. In some examples, the spoofing attack detection status indicates a probability that the image data is from living biological tissue from a human subject or a probability that a spoofing attack is detected.

As example where data source 102 generates image data for an eye of subject 103, liveness measurement unit 104 processes the image data to detect changes in tissue deformation of the eye of subject 103 over time and/or over a spatial volume. For example, liveness measurement unit 104 may detect one or more of spatiotemporal eyeball trajectories and accompanying tissue deformations or curtaining, iris dynamics and/or blood flow in and around the iris. Liveness detection unit 104 analyzes the detected changes to determine whether the image data is representative of the behavior of live, human tissue or whether the representative of non-human or non-live tissue, thereby indicating a spoofing attack. For example, liveness measurement unit 104 may analyze the three-dimensional structure of dynamic folding and unfolding of the iris as the pupil contracts or dilates, including ruffling, occlusion, and anisotropic and/or spatially varying patterns of contraction and dilation to detect changes that are representative of the behavior of live, human tissue. Because the movement of such structural features may be extremely difficult or impossible to reproduce artificially, by detecting such changes in the tissue over time, over spatial volume, or a combination of both, liveness measurement unit 104 may provide reliable and accurate differentiation of live, human tissue from artificial devices used in a spoofing attack.

As an example where data source 102 generates image data for a face of subject 103, liveness measurement unit 104 processes the image data to detect changes in tissue deformation or skin wrinkling of the face or regions of the face of subject 103 over time or over spatial volume. For example, liveness measurement unit 104 may detect one or more of local blood flow responses or micro-sweat responses of facial regions of subject 103. As a further example, liveness measurement unit 104 may analyze wrinkling and stretching of skin regions of the face of subject 103 to determine whether the imaged tissue deforms in a similar manner to that expected of live, human skin. For example, liveness measurement unit 104 may analyze wrinkling and folding of skin over time at sufficiently fine spatial and/or temporal resolutions such that the imaged microscopic structural features may be impractical or impossible difficult to mimic successfully via manufactured or artificial processes. For example, the spatial resolution of the skin may be sufficient to track pores, hair follicles, or imperfections of the skin during wrinkling and/or folding of the skin. In other examples, liveness measurement unit 104 may analyze subject 103 for facial expression and/or speaking dynamics (e.g., such as lip movement or shape during phoneme pronunciation). Such techniques may further prevent the use of mutilation or surgical techniques to spoof the biometric security system, because the response properties of such surgically altered tissues, including stretching/wrinkling patterns of facial skin, may be detectable at the small scales used by liveness measurement unit 104.

As an example where data source 102 generates image data for a finger of subject 103, liveness measurement unit 104 processes the image data to detect changes in tissue deformation of the finger. For example, liveness measurement unit 104 may analyze changes in a deep fingerprint of subject 103, changes between multiple sub-surface dermal layers in a topography of sub-surface dermal layers of the finger, changes in surface fingerprint ridge structures of the finger, or detect a response of physiologically active structures such as, e.g., filling or emptying of sweat glands or blood vessel deformation due to blood flow, heartbeat, pulsation, vasodilation and/or vasocontraction.

As one example, subject 103 may place a finger on a glass plate of a fingerprint scanner. While maintaining contact of a fingertip with the glass plate, subject 103 pushes the finger forward or backward parallel to the surface of the plate. Data source 102 generates image data of the finger as subject 103 moves the finger as described above. Liveness measurement unit 104 may detect changes in fingerprint ridges of the finger that result from shearing forces imparted when subject 103 moves the finger as described above. Such changes in fingerprint ridges may be extremely difficult to replicate artificially. Therefore, system 100 may use the presence of such changes in fingerprint ridges to determine that the finger is living biological tissue from a human subject.

In some examples, system 100 may store, in a database (not depicted), a profile for each individual authorized to access environment 110. In such an example, each profile stores characteristics unique to the individual, such as specific patterns of folding or curtaining of an iris of that individual, facial expressions, or skin wrinkling. Liveness detection unit 104 may use biometric information indicative of an identify of subject 103 obtained by biometric identification unit 105 to retrieve a profile corresponding to the identity of subject 103. Liveness detection unit 104 may compare detected changes in structure features in the tissue to characteristics within the profile to determine whether the imaged tissue is from living biological tissue from the same person identified by biometric identification unit 105, from a different but live person, or a spoofing attack.

Biometric identification unit 105 processes at least a portion of the same image data generated by data source 102 for the tissue region of subject 103 and used for liveness detection to also generate biometric information indicative of an identity of subject 103. For example, biometric identification unit 105 performs fingerprint scanning, retinal scanning, or facial recognition. In one example, biometric identification unit 105 may be a commercially available face/iris capture device (e.g., the "Eyen," manufactured by Princeton Identity of Hamilton, N.J.), and/or a commercial single finger fingerprint sensor.

In some examples, biometric identification unit 105 may process high resolution image data to detect one or more structural features that uniquely identify subject 103. For example, and with respect to the iris, a detailed time course of the pupillary response, and at sufficient spatial and depth scales, the three-dimensional structure of the folding and unfolding of the iris tissues in depth may be used to uniquely identify subject 103. An iris of each individual may exhibit unique patterns during contraction and dilation, such as, e.g., ruffling, occlusion, and anisotropic and/or spatially varying patterns of contraction and dilation.

Authorization unit 106 may be configured to receive the spoofing attack detection status from liveness measurement unit 104 and the biometric information indicative of the identity of subject 103 from biometric identification unit 105. Authorization unit 106 uses the spoofing attack detection status and biometric information to output an authorization status for subject 103 to access control unit 108. For example, when both the spoofing attack detection status indicates that living biological tissue from a human subject is detected and the biometric information is indicative of an identity of an authorized subject, authorization unit 106 outputs an authorization status indicating that subject 103 is permitted to access environment 110. In contrast, if either the spoofing attack detection status indicates that the imaged tissue is not from a live human subject or if the biometric information is not indicative of an identity of an authorized subject, authorization unit 106 outputs an authorization status indicating that subject 103 is not permitted to access environment 110.

Access control unit 108 controls access to environment 110 in response to the authorization status output received from authorization unit 106. For example, access control unit 108 prevents access to environment 110 when the authorization status indicates that a spoofing attack is detected or that the biometric information is not indicative of an identity of an authorized subject. Further, access control unit 108 allows access to the environment when the authorization status indicates both that living biological tissue from a human subject is detected and that the biometric information is indicative of an identity of an authorized subject. In some examples, access control unit includes a display that outputs an alert when the authorization status indicates that a spoofing attack is detected. Environment 110 may be physical (e.g., a physical building or room), virtual (e.g., a computing environment such as a software program or features of a program, or financial information or a financial account). In this manner, access control unit 108 may control physical access to environment 110 (e.g., via a door or gate) or virtual access to a virtual environment 110 (e.g., via denial of access to a memory, repository, or software features). In other examples, access control unit 108 may not prevent a subject from accessing environment 110, but access control unit 108 may log authorized and non-authorized access to environment and/or alert authorities if non-authorized subjects have accessed environment 110.

In some examples, system 100 further includes stimulus unit 112. Stimulus unit 112 provides a stimulus to subject 103 to evoke a physiological response from subject 103. In the above example, liveness measurement unit 104 processes the image data to detect changes in one or more structural features of the tissue region of subject 103 that occur in response to the stimulus. Liveness measurement unit 104 detects a spoofing attack by correlating the detected changes that occur in response to the stimulus to expected responses to the stimulus. For example, if the detected changes that occur in response to the stimulus exhibit behavior associated with live human tissue, liveness measurement unit 104 generates a spoofing attack detection status that indicates that the image data is from living biological tissue from a human subject.

In some examples, stimulus unit 112 includes a light source that emits light into an eye of subject 103, a speaker that delivers an acoustic stimulus to subject 103, or a motor that delivers a tactile or vibratory stimulus to subject 103. In some examples, stimulus unit 112 includes an electrical stimulation generator that delivers an electrical stimulus to subject 103. In some examples, the electrical stimulus may be sub-threshold electrical stimulus (e.g., an electrical stimulus that is not perceptible to subject 103). In some examples, stimulus unit 112 includes a heating, ventilation, and air conditioning (HVAC) unit that delivers heated or chilled air to subject 103, thereby inducing filling of sweat glands, vasodilation, or vasoconstriction. In some examples, stimulus unit 112 includes a user interface that instructs subject 103 to perform a specific task, such as applying sufficient pressure to a finger to induce blanching, changing orientation or rotating of a body part, performing an activity that affects local blood flow, sweat response, or movement, or changing facial expression (e.g., instructing subject 103 to make a neutral face, and then smile).

Changes in structural features of tissue that occur in response to spatial or temporal stimuli that invoke both autonomic or voluntary neuro-muscular processes may be easily detectable by data source 102 yet extremely difficult to reproduce artificially. Thus, by using stimulus unit 112, system 100 may employ extremely robust detection measures against spoofing and/or presentation attacks.

Biometric access control system 100, as described above, may be used to increase the robustness of biometric control access and provide a higher level of security against spoofing and/or presentation attacks over conventional systems that rely only on static imagery of tissue. Biometric access control system 100 may be used, for example, within a biometric security station that controls access into a secure area or environment, such as within a government or corporate facility. Further, biometric access control system 100 may be used for screening in a high-volume or high-throughput traffic area, such as within a screening process at a mass transit station, an airport, or a sports stadium.

While the biometric access control system 100 of FIG. 1 is described with respect to biometric security for human beings, the techniques of the disclosure may be applied to a variety of applications where the differentiation of living, biological tissue from presentation or spoofing attacks is important. For example, in animal competitions, such as horse racing, dog racing, dog shows, or state fair exhibitions, infected animals may spread disease to other animals and/or humans. To prevent the spread of disease and to verify that an animal is healthy, officials typically require an animal owner to provide documentation certifying the health of the animal. However, this documentation may be "spoofed" for a first, sick animal by presenting documentation that belongs to a second, healthy animal. The techniques of the disclosure described herein may further be used to prevent such spoofing. For example, system 100 may be used to uniquely identify an animal such that an official may determine that presented documentation correctly corresponds to a presented animal.

As a specific example where system 100 is used for liveness and biometric identification of an animal, an animal owner presents a horse and documentation that the horse is healthy. In this example, the documentation further specifies a unique iris identifier for a horse to which the documentation corresponds. Data source 102 generates image data an iris of the presented horse. Liveness measurement unit 104 processes the image data to detect changes over time in the iris of the presented horse, such as folding or curtaining of the iris. Liveness measurement unit 104 generates, based on the detected changes, a unique iris identifier. Liveness detection unit 104 compares the unique iris identifier generated from the image data to the unique iris identifier specified by the documentation. In response to determining that the unique iris identifiers match, liveness detection unit 104 may output a status verifying that the documentation correctly corresponds to the presented horse. In response to determining that the unique iris identifiers do not match, liveness detection unit 104 may output a status indicating that the documentation is for a different animal other than the presented horse.

Figure 2:
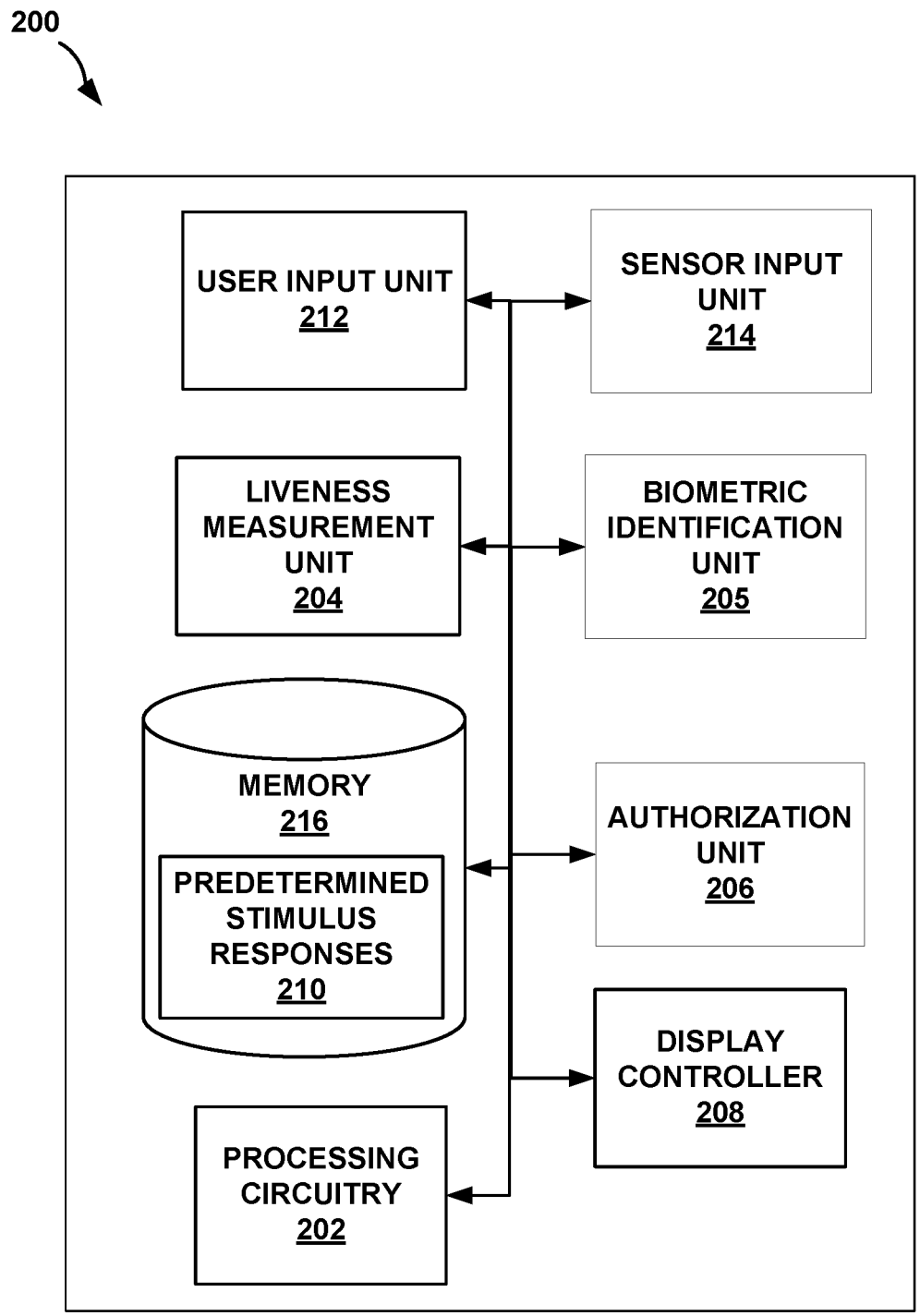
FIG. 2 is a block diagram illustrating an example computing device for controlling access to an environment based on an authorization status of a human subject in accordance with the techniques of the disclosure.

FIG. 2 is a block diagram illustrating an example computing device 200 for controlling access to an environment 110 based on an authorization status of a human subject 103 in accordance with the techniques of the disclosure. Computing device 200 includes user input unit 212, sensor input unit 214, display controller 208, liveness measurement unit 204, biometric identification unit 205, authorization unit 206, memory 216, and processing circuitry 202.

Processing circuitry 202, in one example, is configured to implement functionality and/or process instructions for execution within computing device 200. For example, processing circuitry 202 may be capable of processing instructions stored in memory 216. Examples of processing circuitry 202 may include, any one or more of a microprocessor, a controller, a digital signal processor (DSP), an application specific integrated circuit (ASIC), a field-programmable gate array (FPGA), or equivalent discrete or integrated logic circuitry.

Memory 216 may be configured to store information within computing device 200 during operation. Memory 216, in some examples, is described as a computer-readable storage medium. In some examples, memory 216 is a temporary memory, meaning that a primary purpose of memory 216 is not long-term storage. Memory 216, in some examples, is described as a volatile memory, meaning that memory 216 does not maintain stored contents when the computer is turned off. Examples of volatile memories include random access memories (RAM), dynamic random access memories (DRAM), static random access memories (SRAM), and other forms of volatile memories known in the art. In some examples, memory 216 is used to store program instructions for execution by processing circuitry 202. Memory 216, in one example, is used by software or applications running on computing device 200 to temporarily store information during program execution.

Memory 216, in some examples, also include one or more computer-readable storage media. Memory 216 may be configured to store larger amounts of information than volatile memory. Memory 216 may further be configured for long-term storage of information. In some examples, memory 216 includes non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

In the example of FIG. 2, memory 216 stores one or more predetermined stimulus responses 210. In some examples, each predetermined stimulus response 210 specifies criteria expected for responses by live human tissue to a particular stimulus from stimulus unit 112 of FIG. 1. For example, stimulus unit 112 provides a stimulus to subject 103 to evoke a physiological response from subject 103. Liveness measurement unit 104 processes image data of one or more structural features of a tissue region of subject 103 to detect changes in the one or more structural features that occur in response to the stimulus. Liveness measurement unit 104 correlates the detected changes in that occur in response to the stimulus to predetermined stimulus response 210 to determine whether the detected changes are indicative of living biological tissue from a human subject or indicative of a spoofing attack.

Computing device 200, in one example, also includes user input unit 212. User input unit 212, in some examples, is configured to receive input from a user through tactile, audio, or video feedback. Examples of user interface devices (s) 212 include a presence-sensitive screen (which may also include a display), a mouse, a keyboard, a voice responsive system, video camera, microphone or any other type of device for detecting a command from a user. In some examples, a presence-sensitive display includes a touch-sensitive screen.

Computing device 200, in some examples, includes sensor input unit 214. Sensor input unit 214 is configured to receive electrical signal input from one or more sensors, such as data source 102, and convert the electrical signal input into a form usable by computing device 200. For example, sensor input unit 324 may include software or hardware configured to convert a received signal input from an analog signal to a digital signal. In another example, sensor input unit 214 may include software or hardware configured to compress, decompress, transcode, encrypt, or decrypt a received signal input into a form usable by computing device 200.

Display controller 208 may also be included in computing device 200. Display controller 208, in some examples, is configured to control an output device to provide output to a user using video stimuli. Display controller 208, in one example, includes software or hardware for controlling a video graphics adapter card or a display screen. In other examples, display controller controls output devices such as a cathode ray tube (CRT) monitor, a liquid crystal display (LCD). In another example, instead of controlling a display to provide visual output to a user, display controller 208 controls a sound card, a speaker, or a presence-sensitive display to provide audio or tactile output to a user. In still further examples, display controller 208 is configured to control any other type of output device for converting a signal into an appropriate form understandable to humans or machines or any type of device that can generate intelligible output to a user.

Computing device 200 may further include liveness measurement unit 204, biometric identification unit 205, and authorization unit 206. Each of liveness measurement unit 204, biometric identification unit 205, and authorization unit 206 may include software, hardware, circuitry, or a combination thereof configured to perform the functions of liveness measurement unit 104, biometric identification unit 105, and authorization unit 106 of FIG. 1, respectively. Computing device 200 may include additional or alternative components in other examples. For example, computing device 200 may include a communication unit configured to send or receive information between other computing devices via direct communication and/or networked communication. Although the components of computing device 200 may be hardwired together, one or more components of computing device 200 may be wirelessly connected to computing device 200 (e.g., one or more sensors may transmit data wirelessly to computing device 200).

Figure 3:
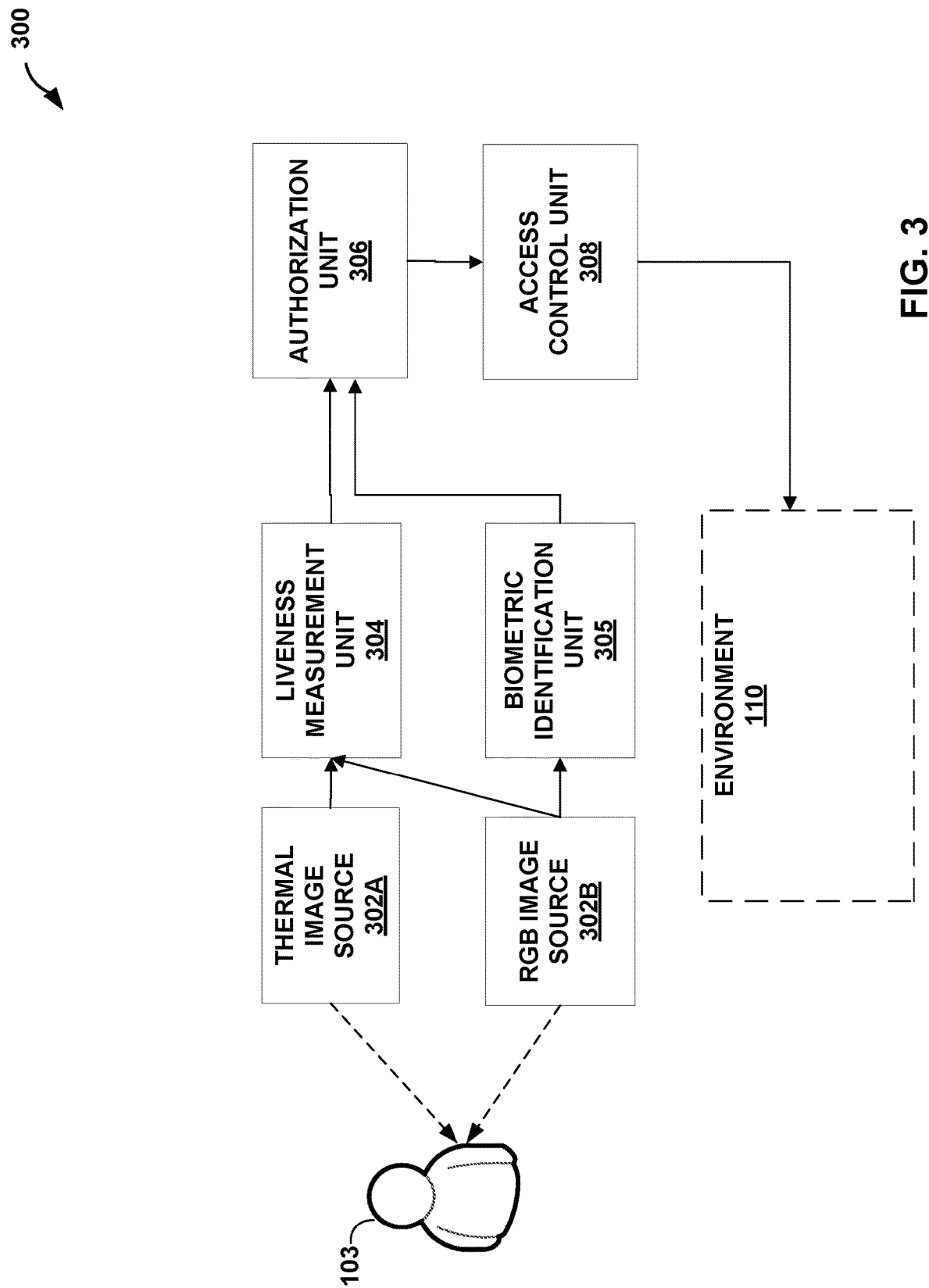
FIG. 3 is a block diagram illustrating another example biometric access control system for controlling access to an environment based on an authorization status of a human subject in accordance with the techniques of the disclosure.

FIG. 3 is a block diagram illustrating another example biometric access control system 300 for controlling access to an environment 110 based on an authorization status of a human subject 103 in accordance with the techniques of the disclosure. System 300 includes thermal image source 302A, RGB image source 302B, liveness measurement unit 304, biometric identification unit 305, authorization unit 306, and access control unit 308. In some examples, system 300 is an example of biometric access control system 100 of FIG. 1. For example, thermal image source 302A and RGB image source 302B may be examples of data source 102 of FIG. 1, liveness measurement unit 304 may be an example of liveness measurement unit 104 of FIG. 1, biometric identification unit 305 may be an example of biometric identification unit 105 of FIG. 1, authorization unit 306 may be an example of authorization unit 106, and access control unit 308 may be an example of access control unit 108 of FIG. 1.

In the example of FIG. 3, RGB image source 302B generates RGB image data of a tissue region of subject 103. In one example, the tissue region is a facial region of subject 103. RGB image source 302B provides the RGB image data to biometric identification unit 305 and liveness measurement unit 304. Biometric identification unit 305 processes the RGB image data to generate biometric information indicative of an identity of subject 103.

Liveness measurement unit 304 processes the RGB image data to identify, based on the RGB image data, to identify, based on the RGB image data, a subregion of the tissue region of subject 103 from which to sense thermal image data. Thermal image source 302A generates thermal image data of the identified subregion of the tissue region of subject 103. Liveness measurement unit 304 processes the thermal image data to detect changes in one or more structural features of the tissue region of subject 103. In some examples, liveness measurement unit 304 detects changes in the one or more structural features over time. In other examples, liveness measurement unit 304 detects changes in the one or more structural features over spatial volume. Liveness measurement unit 104 generates, based on the detected changes in the one or more structural features, a spoofing attack detection status. The spoofing attack detection status indicates either that the thermal image data is from living biological tissue from a human subject or that a spoofing attack is detected.

For example, where the RGB image data is of a face of subject 103, liveness measurement unit 304 processes the RGB image data of the face of subject 103 to identify specific subregions of the face, such as the nares or the philtrum of the nose, from which to sense thermal image data. These portions of the face of subject 103 (e.g., portions of tissue near the nostrils) exhibit repetitive heating and cooling behavior due to breathing of subject 103. Such portions of the face may demonstrate drastically different heating patterns if subject 103 is wearing a mask, such as during a spoofing attack. Furthermore, these heating and cooling patterns of tissue may be very difficult or impossible to accurately mimic artificially. This is generally true even without detecting a temporal breathing pattern because the spatial distribution of temperatures across the face is very repeatable across living subjects, with the highest temperatures at points 705 and 706 of FIG. 7, discussed below. Therefore, such portions of tissue may be suitable for use in system 300 to perform liveness detection.

Figure 4:
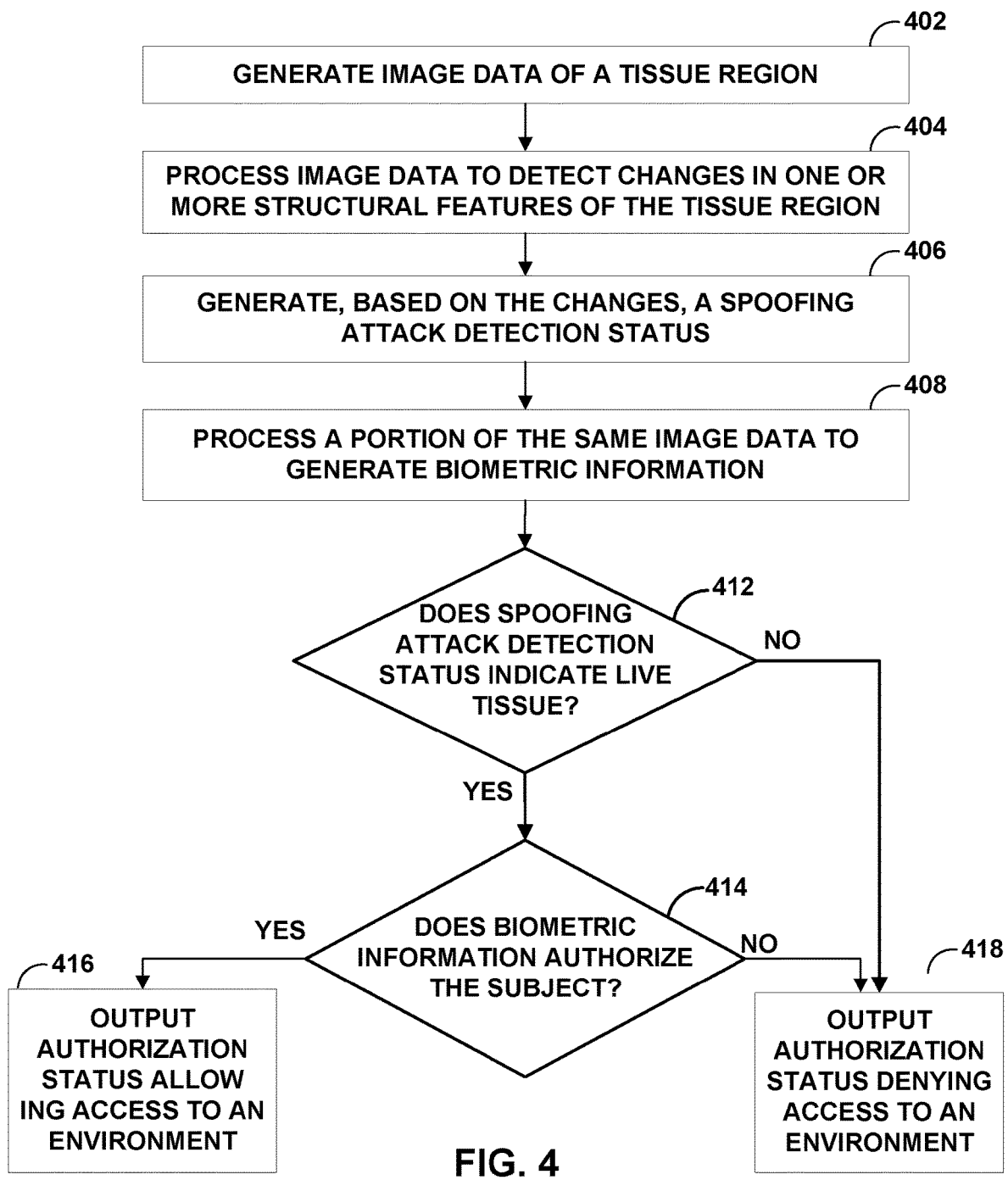
FIG. 4 is a flowchart illustrating an example operation for controlling access to an environment based on an authorization status of a human subject in accordance with the techniques of the disclosure.

FIG. 4 is a flowchart illustrating an example operation for controlling access to an environment based on an authorization status of a human subject in accordance with the techniques of the disclosure. FIG. 4 is described with respect to system 100 described in FIG. 1, but any other system may also perform the features of FIG. 4.

In the example of FIG. 4, data source 102 generates image data of a tissue region of subject 103 (402). In some examples, data source 102 generates image data of structural features of the tissue region of subject 103. In some examples, data source 102 generates two-dimensional image data of the tissue region, while in other examples, data source 102 generates three-dimensional image data of the tissue region. As one example, data source 102 generates hi-resolution three-dimensional OCT image tomography data, which image source provides to liveness measurement unit 104 for liveness detection as discussed below. In this example, data source 102 generates lower-resolution two-dimensional OCT image data, which data source 102 provides to biometric identification unit 105 for biometric identification as discussed below.

Liveness measurement unit 104 processes the image data received from data source 102 to detect changes in one or more structural features of the tissue region of subject 103 (404). In some examples, liveness measurement unit 104 detects changes in one or more structural features that occur over time. In other examples, liveness measurement unit 104 detects changes in one or more structural features that occur over a spatial volume. Liveness measurement unit 104 generates, based on the detected changes in the one or more structural features over the at least one of time or spatial volume, a spoofing attack detection status (406). In some examples, the spoofing attack detection status indicates that the image data is from living biological tissue from a human subject or that a spoofing attack is detected. For example, liveness measurement unit 104 analyzes the changes in the one or more structural features of the tissue region of subject 103 that occur over time to determine whether the changes exhibit behavior indicative of living biological tissue, as is the case if subject 103 is a living, human being, or whether the changes exhibit behavior indicative of artificial or manufactured material, thereby indicating that a spoofing or presentation attack on system 100 is occurring. For example, liveness measurement unit 104 may detect one or more of spatiotemporal eyeball trajectories and accompanying tissue deformations or curtaining, iris dynamics, and/or blood flow in and around the iris of subject 103. In another example, liveness measurement unit 104 may detect one or more of local blood flow responses, micro-sweat responses of facial regions of subject 103 or analyze wrinkling and stretching of skin regions of a face of subject 103. In yet a further example, liveness measurement unit 104 may analyze changes in a deep fingerprint of subject 103, changes between multiple sub-surface dermal layers in a topography of sub-surface dermal layers of the finger, changes in surface fingerprint ridge structures of the finger, or detect a response of physiologically active structures such as, e.g., filling or emptying of sweat glands or blood vessel deformation due to blood flow, heartbeat, pulsation, vasodilation and/or vasocontraction.

Biometric identification unit 105 processes at least a portion of the same image data generated by data source 102 for the tissue region of subject 103 to generate biometric information indicative of an identity of subject 103 (408). For example, biometric identification unit 105 performs fingerprint scanning, retinal scanning, or facial recognition on at least a portion of the same image data analyzed by liveness measurement unit 104 to generate the biometric information indicative of the identity of subject 103.

Authorization unit 106 receives, from liveness measurement unit 104, the spoofing attack detection status. Further, authorization unit 106 receives, from biometric identification unit 205, the biometric information indicative of the identity of subject 103. Authorization unit 106 determines whether the spoofing attack detection status indicates that the image data is from living biological tissue from a human subject (412). In response to determining that the spoofing attack detection status indicates that the image data is not from living biological tissue from a human subject (e.g., "NO" block of 412), then authorization unit 106 outputs to access control unit 108 an authorization status denying access to environment 110 to subject 103 (418).

In response to determining that the spoofing attack detection status indicates that the image data is from living biological tissue from a human subject (e.g., "YES" block of 412), then authorization unit 106 determines whether the biometric information indicative of the identity of subject 103 authorizes subject 103 to access environment 110 (414). In response to determining that the biometric information indicative of the identity of subject 103 does not authorize subject 103 to access environment 110 (e.g., "NO" block of 414), then authorization unit 106 outputs to access control unit 108 an authorization status denying access to environment 110 to subject (418). In response to determining that the biometric information indicative of the identity of subject 103 authorizes subject 103 to access environment 110 (e.g., "YES" block of 414), then authorization unit 106 outputs to access control unit 108 an authorization status allowing access to environment 110 to subject (416).

FIG. 4 describes an example of how system 100 may operate to control access to environment 110. However, system 100 may operate with one or more variations on the example of FIG. 4. For instance, system 100 may perform certain functions in different order, such as generating biometric information (408) prior to processing the image data to detect changes in one or more structural features of the tissue region (406). In other examples, system 100 may not even generate the biometric information if the spoofing attack detection status first indicates a spoof, or, conversely, system 100 may not determine the spoofing attack detection status if biometric identification unit 105 first determines that the subject is not authorized access to the environment.

This iterative processing approach may improve the efficiency of system 100. In other examples, system 100 may perform additional processes, such as processing image data at multiple tissue sites for structural feature changes and/or utilizing image data from multiple tissue sites for biometric information. System 100 may also control access to environment 110 using fewer processes than those shown in FIG. 4. For example, processes 412 and 414 may be combined into a single step that analyzes both the spoofing attack detection status and the biometric information. In another example, system 100 may not generate biometric information indicative of the identity of the subject (408). System 100 may receive the biometric information from a different system or device, or system 100 may not even consider biometric information. For example, system 100 may control access to environment 110 based on the spoofing attack detection status which indicates liveness of the subject instead of, or without the use of, the biometric information indicative of the identity of the subject.

Figure 5:
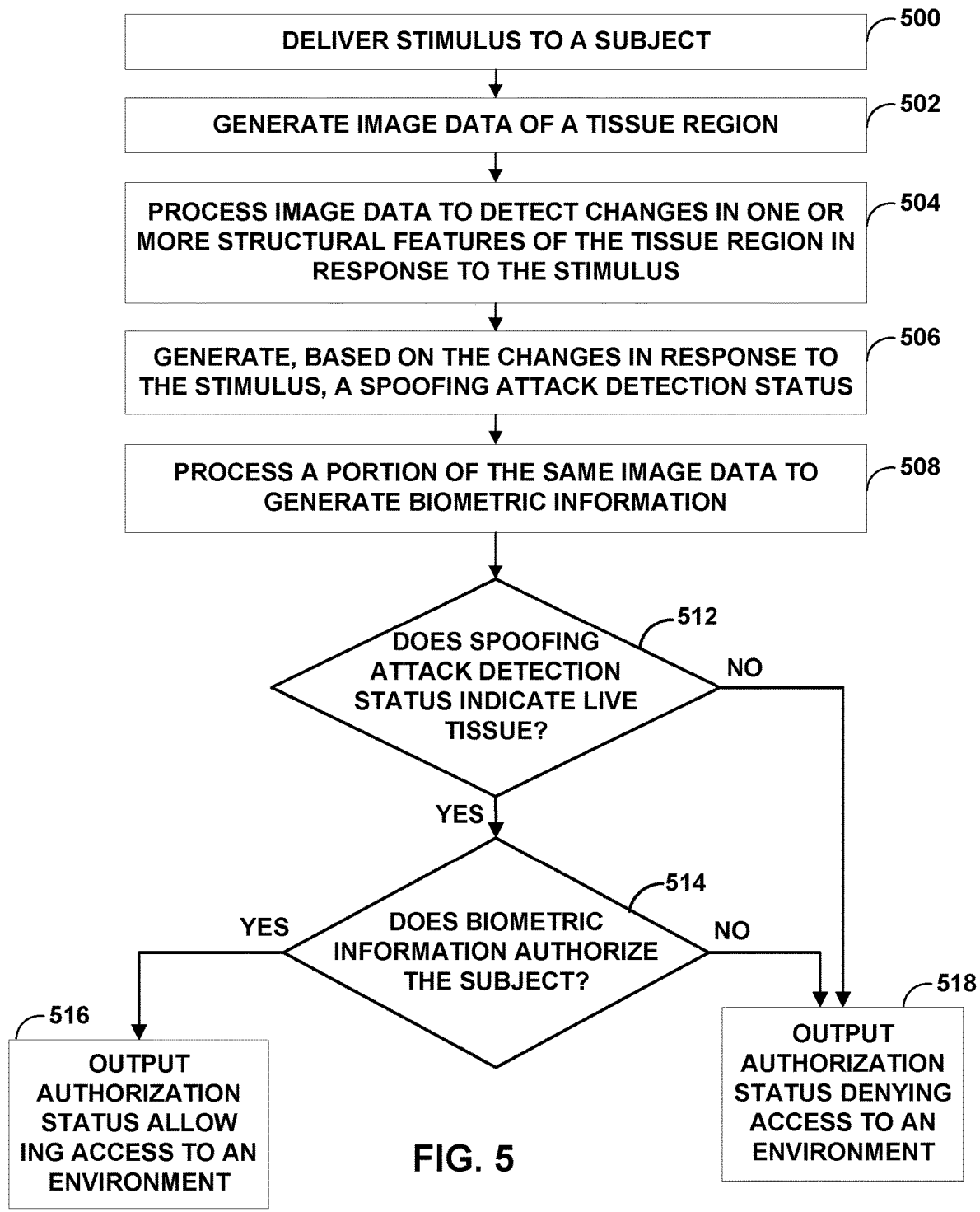
FIG. 5 is a flowchart illustrating an example operation for controlling access to an environment based on an authorization status of a human subject in accordance with the techniques of the disclosure.

FIG. 5 is a flowchart illustrating an example operation for controlling access to an environment based on an authorization status of a human subject in accordance with the techniques of the disclosure. For convenience, FIG. 5 is described with respect to system 100 of FIG. 1.

In the example of FIG. 5, stimulus unit 112 delivers a stimulus to subject 103 to evoke a physiological response from subject 103 (500). In some examples, stimulus unit 112 includes a light source that emits light into an eye of subject 103, a speaker that delivers an acoustic stimulus to subject 103, or a motor that delivers a tactile or vibratory stimulus to subject 103. In some examples, stimulus unit 112 includes an electrical stimulation generator that delivers an electrical stimulus to subject 103. In some examples, the electrical stimulus may be sub-threshold electrical stimulus (e.g., an electrical stimulus that is not perceptible to subject 103). In some examples, stimulus unit 112 includes a user interface that instructs subject 103 to perform a specific task, such as applying sufficient pressure to a finger to induce blanching, changing orientation or rotating of a body part, performing an activity that affects local blood flow, sweat response, or movement, or changing facial expression (e.g., instructing subject 103 to make a neutral face, and then smile).

Data source 102 then generates image data of a tissue region of subject 103 that captures the response to the stimulus (502). In some examples, data source 102 generates image data of structural features of the tissue region of subject 103. In some examples, data source 102 generates two-dimensional image data of the tissue region, while in other examples, data source 102 generates three-dimensional image data of the tissue region. As one example, data source 102 generates hi-resolution three-dimensional OCT image tomography data, which image source provides to liveness measurement unit 104 for liveness detection as discussed below. In this example, data source 102 generates lower-resolution two-dimensional OCT image data, which data source 102 provides to biometric identification unit 105 for biometric identification as discussed below.

Liveness measurement unit 104 processes the image data received from data source 102 to detect changes in one or more structural features of the tissue region of subject 103 that occur in response to the stimulus (504). In some examples, liveness measurement unit 104 detects changes in one or more structural features that occur over time in response to the stimulus. In other examples, liveness measurement unit 104 detects changes in one or more structural features that occur over spatial volume that occur in response to the stimulus. Liveness measurement unit 104 generates, based on the detected changes in the one or more structural features that occur in response to the stimulus, a spoofing attack detection status (506). In some examples, the spoofing attack detection status indicates that the image data is from living biological tissue from a human subject or that a spoofing attack is detected. For example, liveness measurement unit 104 detects a spoofing attack by correlating the detected changes that occur in response to the stimulus to expected responses to the stimulus (e.g., responses that live tissue of a human being exhibit). For example, if the detected changes that occur in response to the stimulus exhibit behavior associated with live human tissue, liveness measurement unit 104 generates a spoofing attack detection status that indicates that the image data is from living biological tissue from a human subject. In contrast, if the changes exhibit behavior indicative of artificial or manufactured material, liveness measurement unit 104 determines that a spoofing or presentation attack on system 100 is occurring.

Biometric identification unit 105 processes at least a portion of the same image data generated by data source 102 for the tissue region of subject 103 to generate biometric information indicative of an identity of subject 103 (508). For example, biometric identification unit 105 performs fingerprint scanning, retinal scanning, or facial recognition on at least a portion of the same image data to generate the biometric information indicative of the identity of subject 103.

Authorization unit 106 receives, from liveness measurement unit 104, the spoofing attack detection status. Further, authorization unit 106 receives, from biometric identification unit 205, the biometric information indicative of the identity of subject 103. Authorization unit 106 determines whether the spoofing attack detection status indicates that the image data is from living biological tissue from a human subject (512). In response to determining that the spoofing attack detection status indicates that the image data is not from living biological tissue from a human subject (e.g., "NO" block of 512), then authorization unit 106 outputs to access control unit 108 an authorization status denying access to environment 110 to subject 103 (518).

In response to determining that the spoofing attack detection status indicates that the image data is from living biological tissue from a human subject (e.g., "YES" block of 512), then authorization unit 106 determines whether the biometric information indicative of the identity of subject 103 authorizes subject 103 to access environment 110 (514). In response to determining that the biometric information indicative of the identity of subject 103 does not authorize subject 103 to access environment 110 (e.g., "NO" block of 514), then authorization unit 106 outputs to access control unit 108 an authorization status denying access to environment 110 to subject (518). In response to determining that the biometric information indicative of the identity of subject 103 authorizes subject 103 to access environment 110 (e.g., "YES" block of 414), then authorization unit 106 outputs to access control unit 108 an authorization status allowing access to environment 110 to subject (516).

FIG. 5 describes an example of how system 100 may operate to control access to environment 110. However, system 100 may operate with one or more variations on the example of FIG. 5. For instance, system 100 may perform certain functions in different order, such as generating biometric information (508) prior to processing the image data to detect changes in one or more structural features of the tissue region (506). In other examples, system 100 may not even generate the biometric information if the spoofing attack detection status first indicates a spoof, or, conversely, system 100 may not determine the spoofing attack detection status if biometric identification unit 105 first determines that the subject is not authorized access to the environment. This iterative processing approach may improve the efficiency of system 100. In other examples, system 100 may perform additional processes, such as processing image data at multiple tissue sites for structural feature changes and/or utilizing image data from multiple tissue sites for biometric information. System 100 may also control access to environment 110 using fewer processes than those shown in FIG. 5. For example, processes 512 and 514 may be combined into a single step that analyzes both the spoofing attack detection status and the biometric information. In another example, system 100 may not generate biometric information indicative of the identity of the subject (508). System 100 may receive the biometric information from a different system or device, or system 100 may not even consider biometric information. For example, system 100 may control access to environment 110 based on the spoofing attack detection status which indicates liveness of the subject instead of, or without the use of, the biometric information indicative of the identity of the subject.

Figure 6:
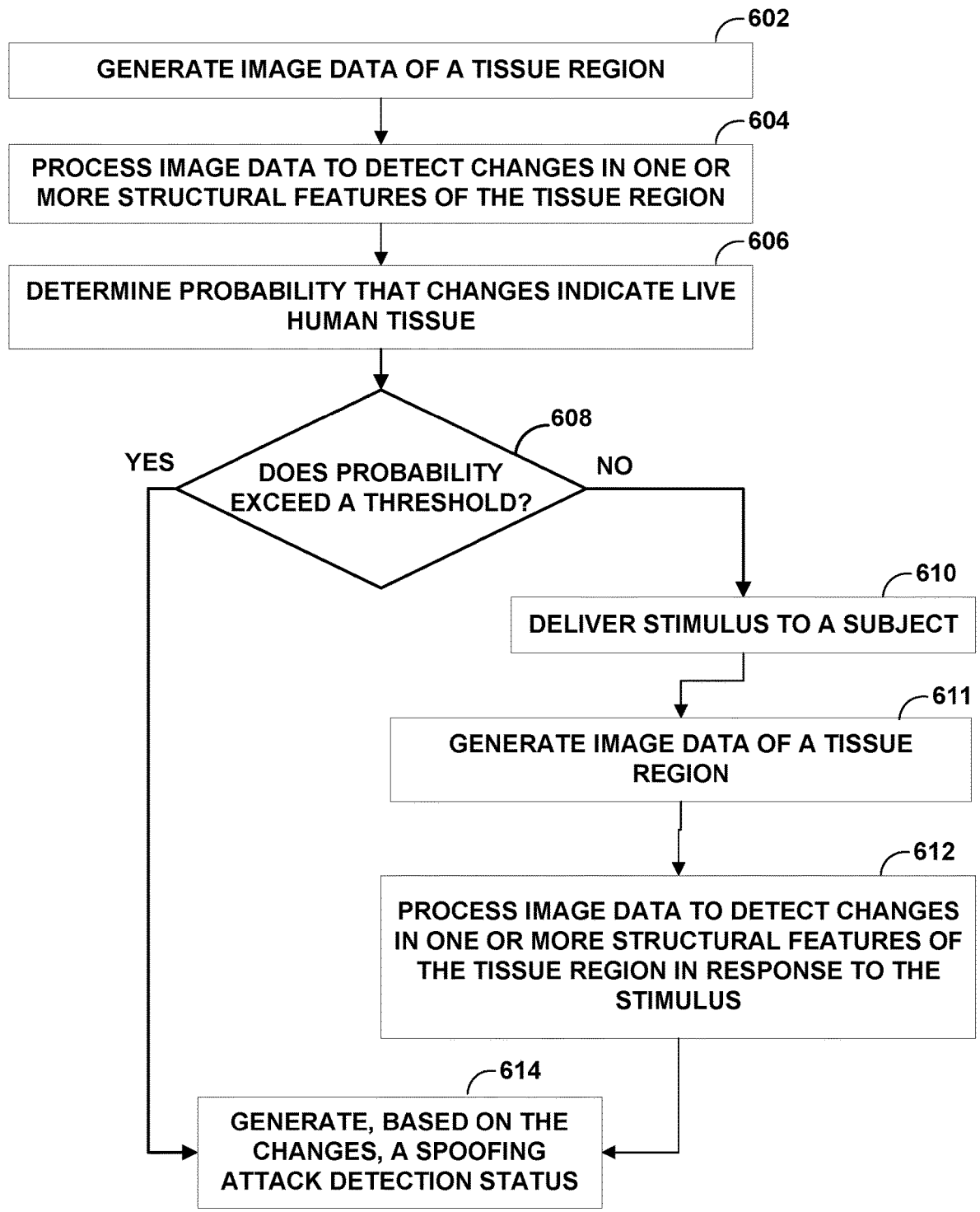
FIG. 6 is a flowchart illustrating an example operation for processing image data to detect changes in one or more structural features of a tissue region of a subject and generating, based on the detected changes, a spoofing attack detection status in accordance with the techniques of the disclosure.

FIG. 6 is a flowchart illustrating an example operation for processing image data to detect changes in one or more structural features of a tissue region of a subject and generating, based on the detected changes, a spoofing attack detection status in accordance with the techniques of the disclosure. For convenience, FIG. 6 is described with respect to system 100 FIG. 1.

In the example of FIG. 6, data source 102 generates image data of a tissue region of subject 103 (602). In some examples, data source 102 generates image data of structural features of the tissue region of subject 103. In some examples, data source 102 generates two-dimensional image data of the tissue region, while in other examples, data source 102 generates three-dimensional image data of the tissue region. As one example, data source 102 generates hi-resolution three-dimensional OCT image tomography data, which image source provides to liveness measurement unit 104 for liveness detection as discussed below. In this example, data source 102 generates lower-resolution two-dimensional OCT image data, which data source 102 provides to biometric identification unit 105 for biometric identification as discussed below.

Liveness measurement unit 104 processes the image data received from data source 102 to detect changes in one or more structural features of the tissue region of subject 103 (604). In some examples, liveness measurement unit 104 detects changes in one or more structural features that occur over time. In other examples, liveness measurement unit 104 detects changes in one or more structural features that occur over spatial volume.

Based on the detected changes, liveness measurement unit 104 determines a probability or estimate that the detected changes in the one or more structural features indicate living biological tissue from a human subject (606). Liveness measurement unit 104 determines whether the probability that the detected changes in the one or more structural features indicate living biological tissue from a human subject exceeds a predetermined threshold or predetermined certainty (608). For example, the predetermined threshold may be 50%, 75%, 90%, 95%, 99%, etc. In some examples, the predetermined threshold may be selected based on the intended application of system 100. For example, the cost of a false positive may be very high, such as may be the case for a government facility or to grant access to financial information. In such an example, the predetermined threshold may be set very high (e.g., 99%) to avoid false positives.

In another example, the cost of a false positive may be low, such as may be the case where other secondary measures to catch attackers exist or for use in high-volume or high-throughput scenarios, such as mass transit or airport screening. In such an example, the predetermined threshold may be set low (e.g., 50%) to increase the speed at which people are processed by the system. In another example where the system is implemented on a consumer mobile device, the predetermined threshold may be set even lower to avoid frustration in the user by requiring the user to undergo a lengthy liveness detection process.

In response to determining that the probability that the detected changes in the one or more structural features indicate living biological tissue from a human subject exceeds the predetermined threshold (e.g., "YES" block of 608), liveness measurement unit 104 generates, based on the detected changes in the one or more structural features over the at least one of time or spatial volume, a spoofing attack detection status (614). Because the probability exceeds the predetermined threshold, the spoofing attack detection status would indicate that the one or more structural features indicate living biological tissue from a human subject.

However, in some cases, the probability that the detected changes in the one or more structural features indicate living biological tissue from a human subject may not exceed the predetermined threshold. This may occur, for example, if data source 102 generates poor quality image data or if the changes to the one or more structural features of the tissue region of subject 103 are not conclusive as to whether the one or more structural features are representative of living biological tissue or representative of artificial or manufactured tissue. In this case, liveness measurement unit 104 may require additional information to determine whether or not a spoofing attack is occurring.

Therefore, in response to determining that the detected changes in the one or more structural features indicate living biological tissue from a human subject do not exceed the predetermined threshold (e.g., "NO" block of 608), liveness measurement unit controls stimulation unit 112 to deliver a stimulus to subject 103 to evoke a physiological response from subject 103 (610). In some examples, stimulus unit 112 includes a light source that emits light into an eye of subject 103, a speaker that delivers an acoustic stimulus to subject 103, or a motor that delivers a tactile or vibratory stimulus to subject 103. In some examples, stimulus unit 112 includes an electrical stimulation generator that delivers an electrical stimulus to subject 103. In some examples, the electrical stimulus may be sub-threshold electrical stimulus (e.g., an electrical stimulus that is not perceptible to subject 103). In some examples, stimulus unit 112 delivers the stimulus to the same tissue region imaged by data source 102 with respect to step 602 above. In other examples, stimulus unit 112 delivers the stimulus to a different tissue region than the tissue region imaged by data source 102 with respect to step 602 above. In some examples, stimulus unit 112 includes a user interface that instructs subject 103 to perform a specific task, such as applying sufficient pressure to a finger to induce blanching (e.g., temporarily forcing blood out of the vasculature of the finger), changing orientation or rotating of a body part, performing an activity that affects local blood flow, sweat response, or movement, or changing facial expression (e.g., instructing subject 103 to make a neutral face, and then smile).

Data source 102 generates image data of structural features of the tissue region of subject 103 to capture changes to the tissue region due to the stimulus (611). In some examples, data source 102 generates the image data while stimulation unit 112 delivers the stimulus to subject 103. In other examples, data source 102 generates the image data after stimulation unit 112 delivers the stimulus to subject 103. In some examples, image source generates image data of the same tissue region imaged with respect to step 602 above. In other examples, image source generates image data of a different tissue region than the tissue region imaged with respect to step 602 above.

Liveness measurement unit 104 processes the image data received from data source 102 to detect changes in one or more structural features of the tissue region of subject 103 that occur in response to the stimulus (612). Liveness measurement unit 104 generates, based on the detected changes in the one or more structural features that occur in response to the stimulus, a spoofing attack detection status (614). Liveness measurement unit 104 provides the spoofing attack detection status to authorization unit 106. In some examples, authorization unit 106 may use the spoofing attack detection status to control access by subject 103 to environment 110. In some examples, authorization unit 106 uses the spoofing attack detection status, along with biometric information indicative of an identity of subject 103, to control access by subject 103 to environment 110, as depicted in FIGS. 4 and 5.

Thus, by using the above operation, liveness measurement unit 104 may perform a relatively quick analysis of subject 103 to determine whether the detected changes in the one or more structural features indicate living biological tissue from a human subject or whether the detected changes indicate a presentation attack is occurring. Further, if by using this "quick" analysis, liveness measurement unit 104 is unable to reach a probable determination within a predetermined threshold or certainty, liveness measurement unit 104 may control stimulation unit 112 to deliver a stimulus to subject 103 and analyze the response of the imaged tissue of subject 103 to stimuli before making another, potentially more accurate determination as to whether the detected changes in the one or more structural features indicate living biological tissue from a human subject or whether the detected changes indicate a presentation attack is occurring. In this fashion, an operation as described above may allow system 100 to balance a need for quick throughput of subjects while still providing a high level of security against presentation attacks.

FIG. 6 describes an example of how system 100 may operate to processes image data to detect changes in one or more structural features of a tissue region of a subject and based on the detected changes, generate a spoofing attack detection status. However, system 100 may operate with one or more variations on the example of FIG. 6. For instance, system 100 may perform certain functions in different order, such as generating image data of the tissue region (611) prior to delivering the stimulus to the subject (612). In other examples, system 100 may generate the image data of the tissue region (611) concurrently with delivering the stimulus to the subject (612). In other examples, system 100 may not even deliver the stimulus to the subject (610), generate image data of the tissue region (611), or process the image data to detect the changes in the one or more structural features (612) if, for example, liveness measurement unit 104 determines that the probability is sufficiently low. Such may occur if the probability that the image data of the tissue region is indicative of living biological tissue from a live human subject is so low that the image data is clearly indicative of a spoofing attack on system 100. This iterative processing approach may improve the efficiency of system 100. In other examples, system 100 may perform additional processes, such as processing image data at multiple tissue sites for structural feature changes and/or utilizing image data from multiple tissue sites for biometric information. System 100 may also generate a spoofing attack detection status using fewer processes than those shown in FIG. 6. For example, processes 604 and 606 may be combined into a single step that both processes image data to detect changes in the one or more structural features and determines a probability that the changes are indicative of live human tissue.

Figure 7:
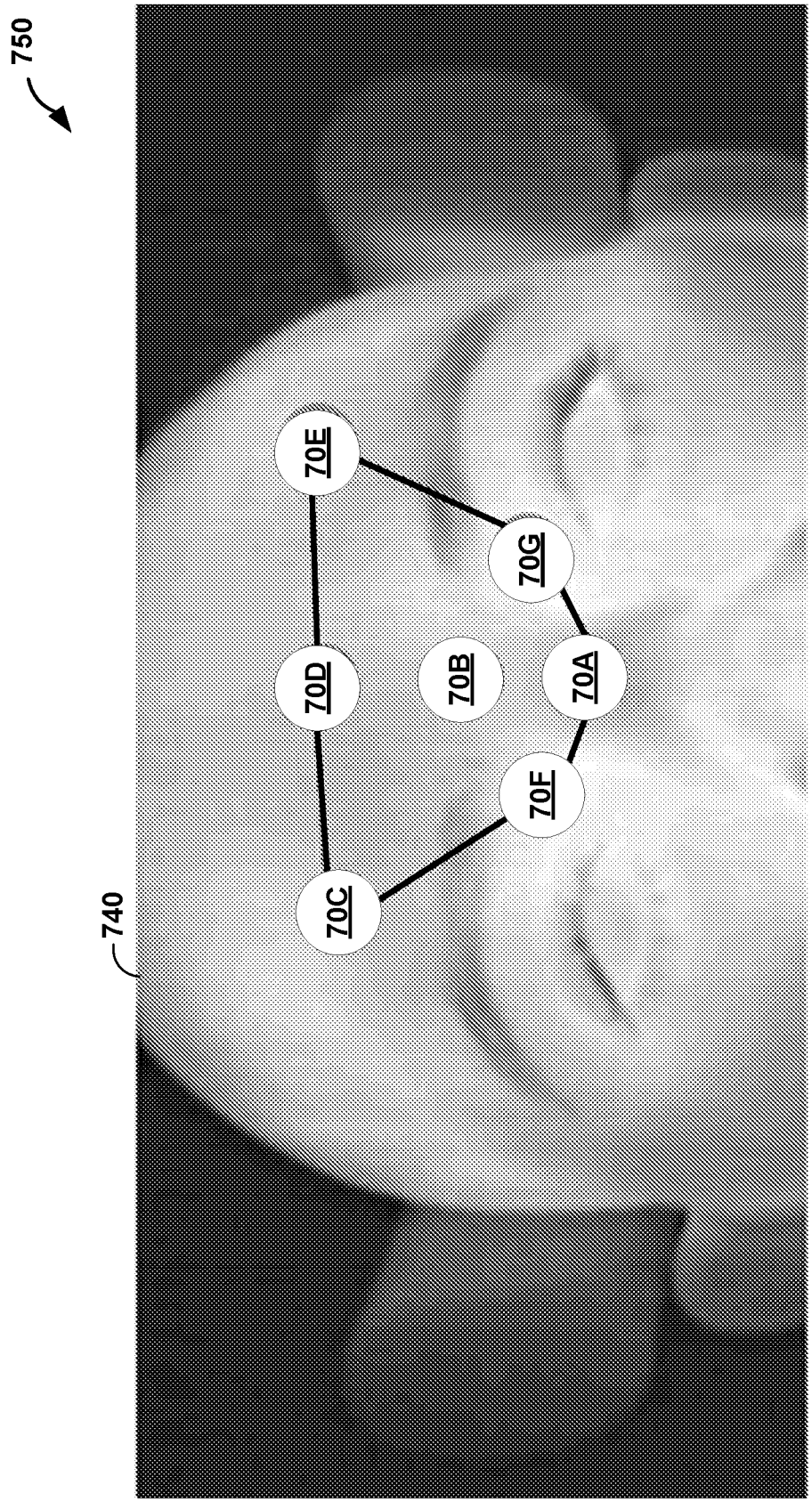
FIG. 7 is an illustration of an example thermal image for use in liveness detection in accordance with the techniques of the disclosure.

FIG. 7 is an illustration of an example thermal image 750 for use in liveness detection in accordance with the techniques of the disclosure. For convenience, FIG. 7 is described with respect to system 100 FIG. 1.

In the example of FIG. 7, thermal image 750 is an example image depicting thermal body heat of a facial region 740 of subject 103. Thermal image 750 identifies portions 70A, 70B, 70C, 70D, 70E, 70F, and 70G (hereinafter, "portions 70") of facial region 740. Particular portions of the face of subject 103 (e.g., portions of tissue near the nostrils or eyes) exhibit repetitive heating and cooling behavior due to breathing of subject 103 or other physiological functions of subject 103. Such portions of the face may demonstrate drastically different heating patterns if subject 103 is wearing a mask, such as during a spoofing attack. Furthermore, these heating and cooling patterns of tissue may be very difficult or impossible to accurately mimic artificially. This is generally true even without detecting a temporal breathing pattern because the spatial distribution of temperatures across facial region 740 of subject 103 may be very repeatable across living subjects, with the highest temperatures at portions 70F and 70G of facial region 740. Therefore, such portions of tissue may be suitable for use in liveness detection, such as by system 300 of FIG. 3, discussed above. However, the example thermal image 750 may also be used for liveness detection in other systems, such as system 100 or computing device 200.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A biometric access control system configured to control access to an environment based on an authorization status of a living subject, the biometric access control system comprising:
   a data source configured to generate image data of a tissue region of a subject;
   a liveness measurement unit configured to process the image data to detect changes over time and a spatial volume in one or more structural features of the tissue region of the subject and generate, based on the detected changes in the one or more structural features, a spoofing attack detection status indicating that the image data is from living biological tissue from a living subject or that a spoofing attack is detected;
   a biometric identification unit configured to process at least a portion of the same image data generated by the data source for the tissue region of the subject to generate biometric information indicative of an identity of the subject; and
   an authorization unit configured to, responsive to the spoofing attack detection status and the biometric information indicative of the identity of the subject, output an authorization status for the subject.

2. The biometric access control system of claim 1, further comprising a stimulus unit configured to deliver a stimulus to the subject,
   wherein the data source configured to generate the image data of the tissue region of the subject is further configured to generate image data of the tissue region of the subject in response to the stimulus, and
   wherein, to process the image data to detect the changes over the spatial volume in the one or more structural features, the liveness measurement unit is further configured to process the image data to detect changes over the spatial volume in the one or more structural features of the tissue region of the subject that occur in response to the stimulus.

3. The biometric access control system of claim 1, wherein, to process the image data to detect the changes over the spatial volume in the one or more structural features, the liveness measurement unit is further configured to process the image data to detect folding or curtaining of an iris of an eye of the subject.

4. The biometric access control system of claim 1, wherein the data source is further configured to generate three-dimensional image data of the tissue region of the subject,
   wherein, to process the image data to detect the changes over spatial volume in the one or more structural features, the liveness measurement unit is further configured to process the three-dimensional image data to detect changes over spatial volume in one or more three-dimensional structural features.

5. The biometric access control system of claim 4, wherein, to process the three-dimensional image data to detect the changes over the spatial volume in the one or more three-dimensional structural features, the liveness measurement unit is further configured to process the three-dimensional image data to detect changes between multiple sub-surface dermal layers in a topography of sub-surface dermal layers of a finger of the subject.

6. The biometric access control system of claim 1, wherein the data source is further configured to generate two-dimensional image data of the tissue region of the subject,
   wherein, to process the image data to detect the changes over the spatial volume in the one or more structural features, the liveness measurement unit is further configured to process the two-dimensional image data to detect changes over spatial volume in one or more two-dimensional structural features.

7. The biometric access control system of claim 1, further comprising an access control unit configured to control access to the environment in response to the authorization status output by the authorization unit by preventing access to the environment when a spoofing attack is detected.

8. The biometric access control system of claim 7, wherein the access control unit includes a display, and wherein the access control unit is further configured to control the display to present an alert indicative of the spoofing attack detection status.

9. The biometric access control system of claim 1, wherein the data source comprises a thermal image sensor configured to generate thermal image data of the tissue region of the subject, and
   wherein the liveness measurement unit configured to process the image data to detect the changes over the spatial volume in the one or more structural features of the tissue region of the subject and generate, based on the detected changes in the one or more structural features, the spoofing attack detection status, is further configured to process the thermal image data to detect thermal changes over at least one of time or spatial volume in one or more structural features of the tissue region of the subject and generate, based on the detected thermal changes in the one or more structural features, the spoofing attack detection status.

10. A biometric detection system comprising:
   a data source configured to generate image data of a tissue region of a subject;
   a liveness measurement unit configured to process the image data to detect changes over time and a spatial volume in one or more structural features of the tissue region of the subject;
   a biometric information unit configured to process the detected changes in the one or more structural features of the tissue region of the subject over the spatial volume to generate biometric information for the subject and output the biometric information for the subject to an external biometric identification unit for processing to determine, based on the biometric information for the subject, an identity of the subject.

11. A method for controlling access to an environment based on an authorization status of a living subject, the method comprising:
   generating, by a data source, image data of a tissue region of a subject;

processing, by a liveness measurement unit, the image data to detect changes over time and a spatial volume in one or more structural features of the tissue region of the subject;

generating, by the liveness measurement unit and based on the detected changes in the one or more structural features, a spoofing attack detection status indicating that the image data is from living biological tissue from a living subject or that a spoofing attack is detected;

processing, by a biometric identification unit, at least a portion of the same image data generated by the data source for the tissue region of the subject to generate biometric information indicative of an identity of the subject; and responsive to the spoofing attack detection status and the biometric information indicative of the identity of the subject, outputting, by an authorization unit, an authorization status for the subject.

12. The method of claim 11, further comprising delivering, by a stimulus unit, a stimulus to the subject,
wherein generating the image data of the tissue region of the subject comprises generating image data of the tissue region of the subject in response to the stimulus, and
wherein processing the image data to detect the changes over the spatial volume in the one or more structural features comprises processing the image data to detect changes over the spatial volume in the one or more structural features of the tissue region of the subject that occur in response to the stimulus.

13. The method of claim 11, wherein processing the image data to detect the changes over the spatial volume in the one or more structural features comprises processing the image data to detect folding or curtaining of an iris of an eye of the subject.

14. The method of claim 11, wherein generating the image data of the tissue region of the subject comprises generating three-dimensional image data of the tissue region of the subject, and
wherein processing the image data to detect the changes over the at least one of time or spatial volume in the one or more structural features comprises processing the three-dimensional image data to detect changes over the spatial volume in one or more three-dimensional structural features.

15. The method of claim 14, wherein processing the three-dimensional image data to detect the changes over the spatial volume in the one or more three-dimensional structural features comprises processing the three-dimensional image data to detect changes between multiple sub-surface dermal layers in a topography of sub-surface dermal layers of a finger of the subject.

16. The method of claim 11, wherein generating the image data of the tissue region of the subject comprises generating two-dimensional image data of the tissue region of the subject, and
wherein processing the image data to detect the changes over the spatial volume in the one or more structural features comprises processing the two-dimensional image data to detect changes over spatial volume in one or more two-dimensional structural features.

17. The method of claim 11, further comprising controlling, by an access control unit, access to the environment in response to the authorization status output by the authorization unit by preventing access to the environment when a spoofing attack is detected.

18. The method of claim 11, wherein generating, based on the detected changes in the one or more structural features, the spoofing attack detection status comprises:
comparing, by the liveness measurement unit, the detected changes over the spatial volume in the one or more structural features to a profile of physiological changes corresponding with the biometric information indicative of the identity of the subject; and
generating, by the liveness measurement unit and based on the comparison of the detected changes to the profile of physiological changes, the spoofing attack detection status.

19. The biometric access control system of claim 1, wherein the detection of changes over time and a spatial volume in one or more structural features of the tissue region of the subject includes detection of movement of at least part of the one or more structural features of the tissue region of the subject.

20. The biometric access control system of claim 11, wherein the detection of changes over time and a spatial volume in one or more structural features of the tissue region of the subject includes detection of movement of at least part of the one or more structural features of the tissue region of the subject.

* * * * *